(12) United States Patent
Jordan

(10) Patent No.: US 6,999,820 B2
(45) Date of Patent: Feb. 14, 2006

(54) WINGED ELECTRODE BODY FOR SPINAL CORD STIMULATION

(75) Inventor: Richard Jordan, N. Little Rock, AR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 10/448,243

(22) Filed: May 29, 2003

(65) Prior Publication Data

US 2004/0243208 A1    Dec. 2, 2004

(51) Int. Cl.
*A61N 1/00* (2006.01)
(52) U.S. Cl. ...................................... 607/117
(58) Field of Classification Search ........ 607/116–117, 607/148; 600/373
See application file for complete search history.

(56) References Cited

U.S. PATENT DOCUMENTS

| | | | | |
|---|---|---|---|---|
| 5,417,719 A | * | 5/1995 | Hull et al. ..................... | 607/46 |
| 5,643,330 A | * | 7/1997 | Holsheimer et al. .......... | 607/46 |
| 6,308,103 B1 | * | 10/2001 | Gielen ........................ | 607/117 |
| 6,319,241 B1 | * | 11/2001 | King et al. .................. | 604/502 |
| 6,514,250 B1 | * | 2/2003 | Jahns et al. ................... | 606/41 |
| 2002/0035377 A1 | * | 3/2002 | Bardy et al. ................... | 607/4 |
| 2002/0111661 A1 | * | 8/2002 | Cross et al. ................. | 607/117 |
| 2003/0204228 A1 | * | 10/2003 | Cross et al. ................. | 607/116 |

FOREIGN PATENT DOCUMENTS

| | | | |
|---|---|---|---|
| WO | 99/56818 | * | 11/1999 |
| WO | 03/090851 | * | 11/2003 |

* cited by examiner

*Primary Examiner*—Mark Bockelman
(74) *Attorney, Agent, or Firm*—Fulbright & Jaworski LLP

(57) ABSTRACT

An implantable stimulation system including epidural lead for spinal cord stimulation that includes a paddle having a curved proximal end and lateral winged tips and an array of electrodes coupled to conductors within a lead body. The conductors couple to a pulse generator or other stimulation device. The curved and winged paddle provides more complete electrical stimulation coverage to targeted human tissue by minimizing the potential gap between electrodes and targeted fibers.

21 Claims, 5 Drawing Sheets

WINGED ELECTRODE BODY FOR SPINAL CORD STIMULATION

TECHNICAL FIELD OF THE INVENTION

The present invention relates generally to implantable medical stimulators and more particularly to an epidural lead having a plurality of electrodes wherein the lead is shaped to optimize electrical coupling between the electrodes and the spinal cord.

BACKGROUND OF THE INVENTION

Electrical stimulation of the spinal cord or peripheral nerves can result in pain reduction and/or elimination. Medical leads having electrodes are often implanted near the spinal column to provide pain relief for chronic intractable pain. The electrodes stimulate tissue within the spinal column to reduce pain sensations at other parts of the body. The stimulation signals applied can be optimized for pain reduction or elimination depending on the location of the pain.

The area of excitation and the intensity of excitation vary according to the stimulation signals. To vary the area of excitation, an array of electrodes implanted near nerve tissue can be configured for a positive, negative, or neutral polarity such that the desired area within the spinal column is electrically stimulated. In addition, the stimulation signal applied on those implanted electrodes can be varied for a corresponding variation in area of excitation within the spinal column and in the intensity of excitation at the pain site.

Prior art electrodes are usually arrayed in a percutaneous or paddle lead. Presently, a percutaneous lead has certain advantages regarding ease of insertion over a paddle lead. However, because of present designs, electrical stimulation with a percutaneous lead occurs 360 degrees around the lead, thereby stimulating posterior portions of the epidural area as well the spinal area and hence, increases unnecessary power consumption.

Paddle leads on the other hand tend to focus the electrical field in only a 180-degree direction in the forward or anterior direction. Because of the electrical field being focused mainly in a single direction, less power is often needed using paddle leads.

Current lead designs suffer in that they often move axially, radially and/or longitudinally in the epidural space after insertion. A cross section of the epidural space can be considered to be an approximate of an isosceles triangular shape with the posterior angle being greater 90 degrees. Additionally, the two "equal angles" tend to drift downwards more anteriorally towards the spinal cord creating a "gutter" effect on the sides of the epidural space, as can be seen in FIG. 3.

Present leads fail to take advantage of the shape of the epidural space. Thus, especially in the case of percutaneous leads, they tend to drift into the side pockets or "gutters" of the epidural space rather than remaining near the centerline. This causes several undesirable effects such as causing greater power consumption in trying to stimulate nerves located near the centerline. Additionally, an unwanted effect of stimulating the nerve root may occur.

Certain paddle leads, such as that described in U.S. patent application Ser. No. 10/025,112, present a curved shaped to match the shape of the dura mater. However, these and other paddle lead designs fail in that their designs do not account for the shape of the epidural space as described above. Hence, they may drift towards one of either gutters and not align a lead in the epidural space. Other limitations in this and other designs will become evident in the detailed discussion of the invention.

What is needed is a lead whose design ensures proper axial placement and thereby maximizes nerve stimulation and minimizes power consumption.

SUMMARY OF THE INVENTION

The present invention provides a lead paddle system and method that substantially eliminates or reduces disadvantages and problems associated with previously developed electrode arrays used for neural stimulation.

More specifically, the present invention provides a winged epidural paddle having a curved outer or posterior surface and a flat inner surface to more efficiently electrically couple the lead to the nervous tissue to be stimulated. Winged edges of the paddle lead are provided to provide for axial alignment within the epidural space.

The present invention provides a solution to the problems of inadequate electrode array coverage by providing a uniquely shaped lead paddle with an array of spaced electrodes or contacts that provide overlapping nerve tissue stimulation.

Accordingly, the present invention provides a unique implantable lead having a curved paddle. The paddle has an outer posterior curved surface to match the shape of the posterior portion of the epidural space and a flat inner or anterior surface to ensure that the maximum space within the epidural space is utilized, thereby preventing axial movement. Winged tips are added to further assist in preventing movement (such as axial or radial movement) within the epidural space and to more approximate the shape of the epidural space. A plurality of electrodes forms an array that transmits stimulation signals to surrounding spinal tissues. The array electrodes overlap in coverage for more complete stimulation of a targeted area. Further, this array can span distant nerve fibers or cover closely packed nerve fibers. Signals to the array can vary on an individual electrode level such that signals applied to each electrode can be controlled to stimulate individual targeted fibers.

The outer curve of the lead approximates the curve of the outside of the epidural space. The inner surface is flat to optimize electrical coupling between the lead and the nerve tissue to be stimulated. Wings on the outer edge of the lead serve to stabilize and immobilize the lead with respect to the targeted tissues and assist in focusing the electrical energy.

The curved paddle of the present invention allows for a better proximity of the stimulating electrodes to the spinal cord, reducing the voltage requirements. Moreover, the winged curved lead paddle ensures that axial or radial migration within the epidural space will not occur, unlike conventional placed leads. Additionally, the winged tips' leading edges are tapered for increased facility of insertion.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the figures, like numerals being used to refer to like and corresponding parts of the various drawings.

An implantable epidural lead for spinal cord stimulation is presented that includes a curved-back and winged-tipped paddle with a flat inner face having an array of electrodes coupled to conductors within a lead body. The conductors couple to a pulse generator or other stimulation device. The curved and winged paddle provides more complete electrical stimulation coverage to targeted human tissue by minimizing the potential gap between electrodes and targeted fibers.

Figure 1:
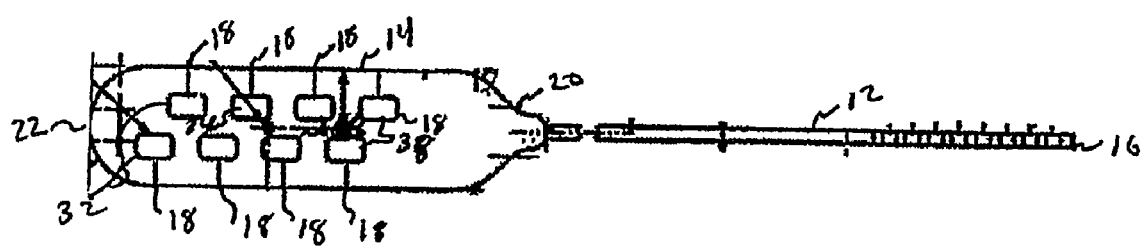
FIG. 1 shows a plan view of a medical lead having a paddle of the present invention coupled to lead bodies.

FIG. 1 provides an illustration of an epidural lead 10 for spinal cord stimulation comprises at least one lead body 12 and a paddle 14. Paddle 14 further comprises an array of electrodes 18 coupled at one end to lead body 12. Lead body 12 further comprises a number of wire conductors. The actual number of wire conductors depends on the number of electrical signals to be generated.

Proximal end 16 of lead body 12 couples to an implantable pulse generator, intermediate wiring, or other stimulation device as known to those skilled in the art. The stimulation pulses produced by the implantable pulse generator travel from the pulse generator through the proximal ends 16 of lead bodies 12, via conductors to distal ends of lead bodies 12, and terminate at electrodes 18 within paddle 14.

Electrodes 18 transmit stimulation pulses to targeted spinal tissue. The structure transmits stimulation pulses from an array of electrodes 18. The configuration of the array is selected through testing of the efficacy of alternate electrode combinations. Alternatively, a single electrode 18 or a plurality of electrodes 18 depending on the desired stimulation can transmit the stimulation pulse.

The epidural lead taught in the disclosure can be employed within fully implantable elements containing a generator 30 or systems employing partially implanted generators or R-F systems.

Each lead 12 is generally a wire metal conductor within an insulating sheath. The insulating sheath is formed of an inert material such as polyurethane or other like materials as known to those skilled in the art.

Paddle 14 has a plurality of electrodes 18 arrayed along its length and across its width. Although eight electrodes 18 are shown in FIG. 1, alternate arrays and numbers of electrodes can be used. Paddle 14 transmits stimulation signals provided by a pulse generator to surrounding spinal tissues. The stimulation signals have specific signal parameters and may be applied to selected contacts 18 within paddle 14. Thus, depending on the desired location and amount of tissue stimulation, the stimulation signals can be controlled and directed to selected electrode contacts for targeted stimulation.

Figure 3:
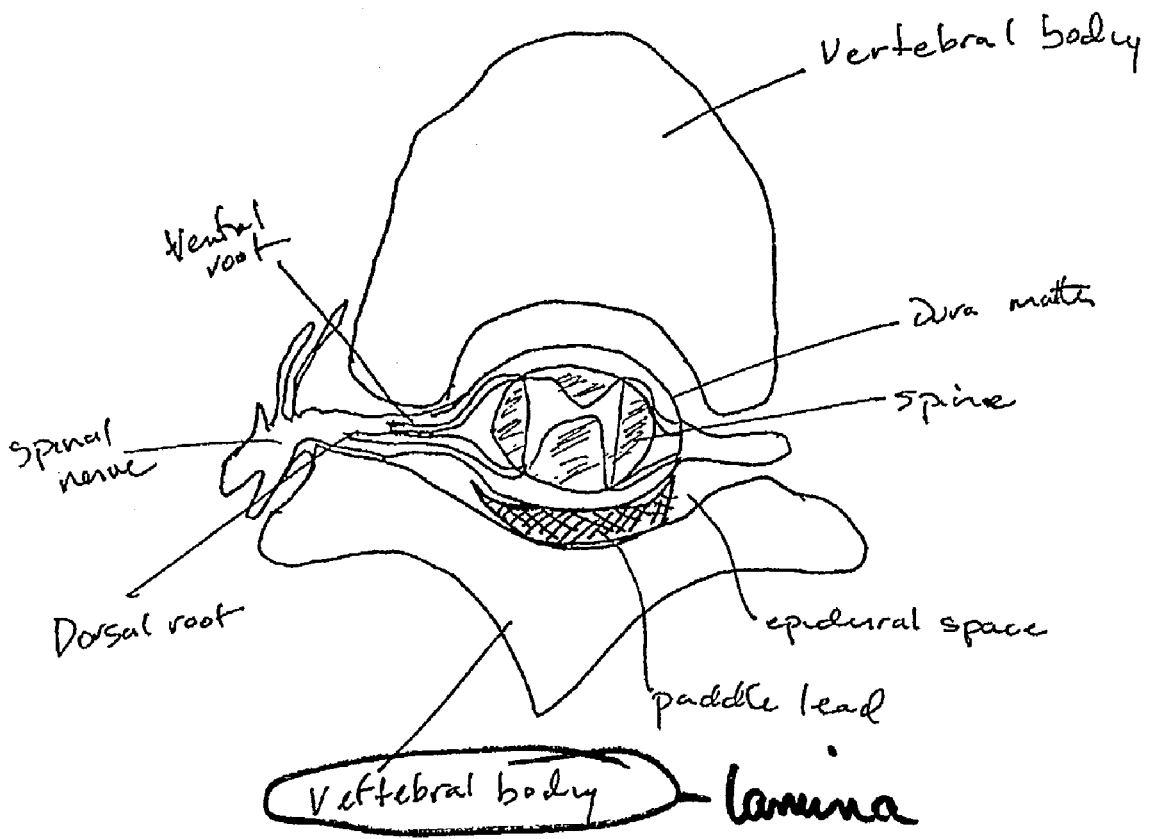
FIG. 3 depicts the paddle placed within the epidural space.

For spinal cord stimulation as shown in FIG. 3, paddle 14 is placed within epidural space 17 outside dura matter 15. Stimulation occurs through dura matter 15 to the spinal cord or other such targeted tissues 19. Outer curve 21 of the paddle 14 matches the posterior shape of epidural space 17, which resembles the shape of an isosceles triangle. This allows the posterior side of the epidural space to assist in containing the paddle 14 flat against the dura mater 15. The flat inner surface 25 allows paddle 14 to sit firmly against the dura mater and more closely interface with the spinal tissues.

Returning to FIG. 1, curved paddle 14 comprises an array of eight electrode contacts 18 spaced axially along the length of curved lead paddle 14 and laterally across the width. This array of electrodes 18 spans distant stimulation points, and at the same time provides overlapping combinations that cover closely packed stimulation points. Any number of electrodes 18 may be placed on paddle 14. Epidural space 17 helps determine the maximum axial width of any implanted body. The axial separation of electrodes 18 within the array must span distant stimulation points to maximize the number of nerve fibers stimulated by the array.

Variations of the spacing of the electrodes 18 and the axial width of the paddle 14 can be empirically determined dependent on the needed stimulation. The thickness of paddle 14 from inner flat portion to outer curved portion requires minimizing the thickness of electrodes and accompanying conductors to reduce the possibility of compression of the spinal cord by paddle 18.

The contact area of electrodes 18 is also minimized, but simultaneously should avoid lesions from higher electrical current densities caused by smaller contact areas. Electrodes may be of any suitable size. As shown in FIG. 1, curved lead paddle 14 takes the shape of a slender elongated paddle.

Paddle 14 may be made of any suitable material as known to those skilled in the art. Such materials may include silicone rubber, adapted to be disposed within the human body. The lead paddle has a proximal end 20 and a distal end 22. Tapered proximal end 20 provides at least one opening 24 for conducts to pass into the lead paddle and couple to electrodes 18. Distal end 22 comprises curved and rounded edges to prevent abrasion of tissues and to ensure safer placement of curved lead paddle. Sides 26 of the curved lead paddle 14 are tapered and also rounded to prevent abrasion of tissue.

Figure 2:
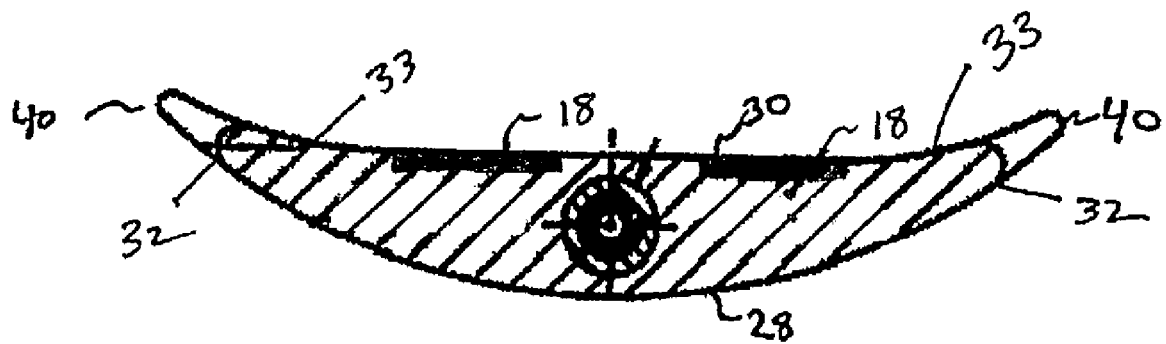
FIG. 2 provides a cross section of the paddle of FIG. 1.

As shown in FIG. 2, outer surface 28 of curved lead paddle 14 curves laterally to match the curvature of the posterior portion of the epidural space. The outer surface 28 presents a curved backside of paddle 14. While the curve is uniform in FIG. 2, those skilled in the art will recognize that the curved backside may present a more triangular or other shape to more particularly conform to the epidural space.

FIG. 2 shows a relatively flat or slightly concave inner face or surface 30, which enhances fiber stimulation by allowing electrodes 18 to be in closer proximity to the dura mater. Electrodes 18 as shown are placed near inner surface 30 to enhance electrical coupling. This close proximity may occur by slightly compressing the dura mater, which places the electrodes in a reduced distance to the desired nerve tissue. The compression may occur because the curved backside fills the epidural space thereby allowing the flat face to exert slight pressure on the dura mater.

FIG. 2 shows the planar orientation of electrodes 18. Electrodes 18 are typically placed as near the flat surface as possible in order to maximize stimulation, however, recessed or protruding electrodes or other orientations of the electrodes relative are contemplated. Importantly, the planar orientation of the electrodes 18 should be relatively parallel to inner flat face in order to maximize stimulation to those nerve fibers nearest the inner flat face.

As is additionally shown in FIG. 2. the outer back surface 28 continues on or extends past the flat surface side or inner surface 30 at point 32. This extension of the curved outer surface 28 past the flat face side or inner surface 30 helps to create wing tips 40. In order to allow safer insertion into the epidural space, the inner surface 30 is formed to meet outer surface 28, at point 33. This allows wing tips 40 to present a more uniform surface area.

Additional methods of construction of the wing tips are envisioned. For example, the wing tips may be added through the manufacturing process to a previously flat paddle lead. In this case the winged tips would be added along the length 24 of a paddle similar to paddle 14. Thus, while a curved back is presented, it is similarly envisioned that the winged tips may be attached to a paddle lead with no curved back. This design could be used on patients where the sizing of the epidural space may not be suitable for a curved back, however, where it would remain desirable to prevent "gutter-drift" of the paddle lead.

A specific electrode configuration is shown in FIG. 1. However, other configurations may be contemplated to allow for stimulation overlap across the width of the paddle with adequate axial spacing. As depicted, electrode pairs 32, 34, 36, and 38 are located on the paddle and positioned near the periphery of the paddle. The pair width is the distance between the electrodes within pair. As shown, no electrodes exist between individual pairs of electrodes, only axially along the lead paddle. In addition, wings 40 as shown in FIG. 2 prevent migration of paddle 14 following implantation.

Figure 4:
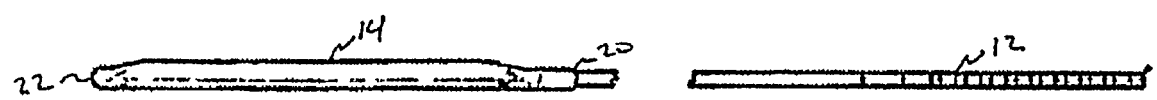
FIG. 4 depicts a side view of the paddle.

FIG. 4 depicts a side view of paddle 14. FIG. 4 shows that the edges of the paddle are curved to allow for ease of insertion and to prevent abrasion during insertion.

Figure 5:
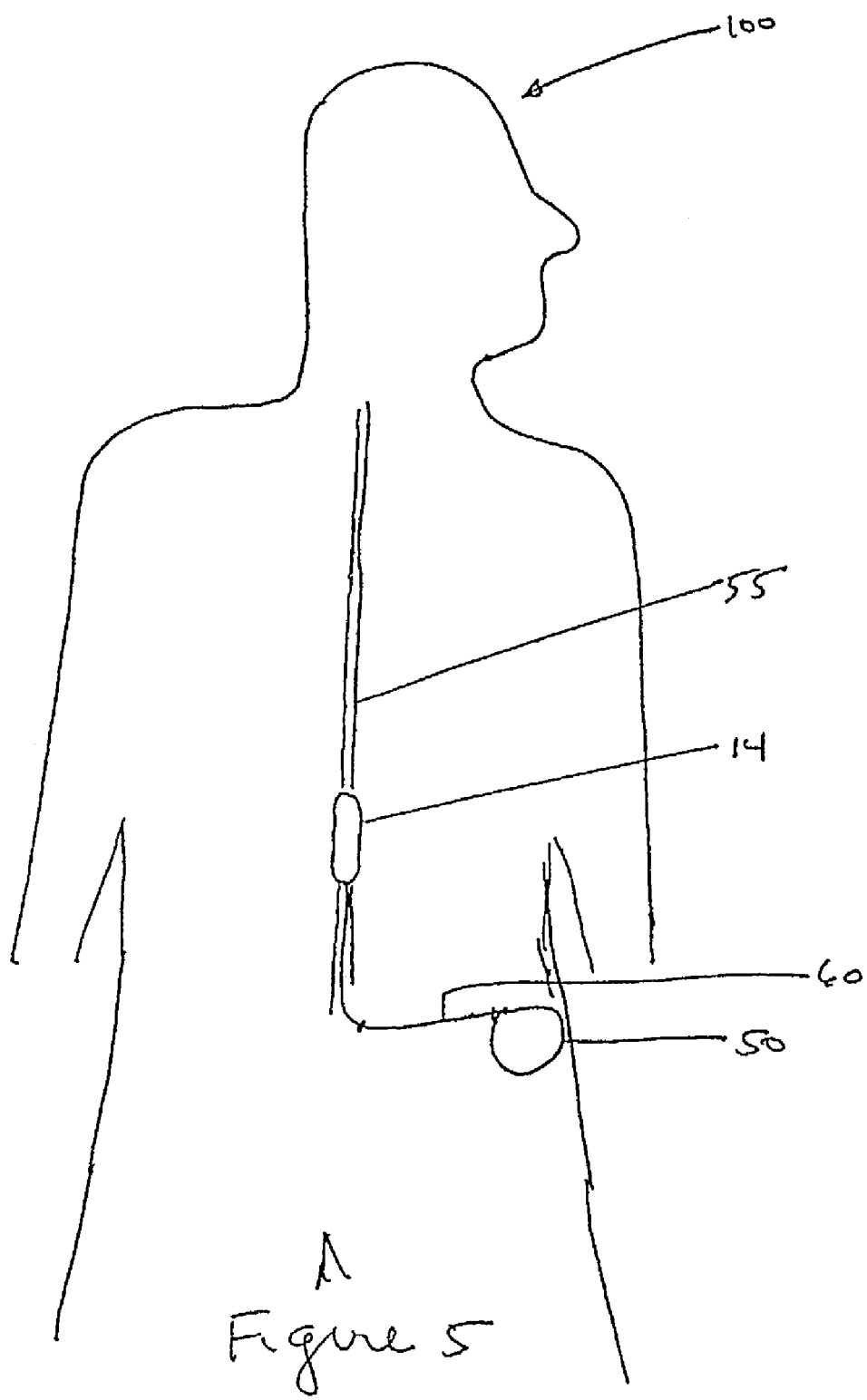
FIG. 5 illustrates the present invention as used within a human body.

FIG. 5 depicts the present invention internalized within human body 100. As shown in FIG. 5, a signal generating means 50 is implanted into a patient. The signal generating means 50 may be an implantable pulse generator or the receiving means (an antennae) of an implantable RF system, as is known in the art. The signal generator 50 is connected to paddle 14, which is implanted in the epidural space of the spine 55 of the patient, via extension cable 60. As is known in the art, the lead may be connected to the signal generator directly without the use of extension cable 60.

In summary, the present invention provides a curved epidural paddle that more efficiently allows electrodes to electrically couple to spinal cord tissue.

Although the present invention is described in detail, it should be understood that various changes, substitutions and alterations could be made hereto without departing from the spirit and scope of the invention.

I claim:

1. An implantable lead for stimulating nerve tissues comprising:
    a plurality of terminals;
    a plurality of electrodes;
    a plurality of conductors coupled to the terminals and electrodes; and
    a paddle shaped body wherein the body comprises:
        a flat face side where the electrodes are exposed;
        a backside opposite of the flat face side; and
        winged tips connected to the backside and the flat face side, wherein the wing tips have curved portions extending from the flat face side such that the curved portions and the flat face side form a concave surface.

2. The implantable lead of claim 1 wherein the backside is curved.

3. The implantable lead of claim 2, wherein the curved backside extends beyond the flat face to form the winged tip.

4. The implantable lead of claim 2, wherein the curved backside has a uniform curve.

5. The implantable lead of claim 2, wherein the curved backside is triangular in shape.

6. The implantable lead of claim 2, wherein the planar orientation of the electrodes are parallel to the inner flat face.

7. The implantable lead of claim 1 wherein the electrodes protrude from the inner flat face.

8. A system for electrical stimulation of nerve tissues, the system comprising:
    a signal generator for generating electrical signals; and
    a paddle lead connectable to the generator for stimulating nerve tissue, the lead comprising:
        a plurality of terminals;
        a plurality of electrodes;
        a plurality of conductors coupled to the terminals and electrodes; and
        a paddle shaped body wherein the body comprises:
            a flat face side where the electrodes are exposed;
            a backside opposite of the flat face side;
            winged tips connected to the backside and the flat face side, wherein the wing tips have curved portions extending from the flat face side such that the curved portions and the flat face side form a concave surface.

9. The system of claim 8, wherein the backside is curved.

10. The system of claim 9, wherein the curved backside extends beyond the flat face to form the winged tip.

11. The system of claim 9, wherein the curved backside has a uniform curve.

12. The system of claim 9, wherein the curved backside is triangular in shape.

13. The system of claim 8, wherein the planar orientation of the electrodes are parallel to the inner flat face.

14. The system of claim 8, wherein the electrodes protrude from the inner flat face.

15. A method of stimulating nerve tissue comprising:
    placing a paddle lead in the epidural space, wherein the paddle comprises:
        a plurality of terminals:
        a plurality of electrodes;
        a plurality of conductors coupled to the terminals and electrodes; and
        a paddle shaped body wherein the body comprises:
            a flat face side where the electrodes are exposed;
            a backside opposite of the flat face side; and
            winged tips connected to the backside and the flat face side, wherein the wing tips have curved portions extending from the flat face side such that the curved portions and the flat face side form a concave surface; and
    generating pulses through the paddle to stimulate nervous tissue.

16. The method of claim 15 further comprising the step of filling the epidural space where the lead is located with the paddle body of the lead.

17. The method of claim 15 further comprising the step of curving the backside of the paddle body.

18. The method of claim 17 further comprising the step of extending the curved portion beyond the flat face side.

19. The method of claim 17 further comprising the step of shaping the curved backside in a triangular shape.

20. The method of claim 15 further comprising the step of orienting the electrodes parallel to the flat face side.

21. An implantable lead for stimulating nerve tissues comprising:

a plurality of terminals;
a plurality of electrodes;
a plurality of conductors coupled to the terminals and electrodes; and
a paddle shaped body wherein the body comprises:
   a substantially flat ventral face portion where the electrodes are exposed;
   an outer surface opposite of the ventral surface portion; and
   winged tips connected to the outer surface and the ventral surface portion, wherein the wing tips have curved portions extending from the ventral surface portion and having a curvature greater than the ventral face portion such that the curved portions and ventral face portion form a concave surface.

* * * * *